(12) United States Patent
Yen et al.

(10) Patent No.: US 10,172,543 B2
(45) Date of Patent: Jan. 8, 2019

(54) METHOD OF MEASURING THE HEART RATE AND RESPIRATORY RATE OF A HUMAN BEING

(71) Applicants: Nelson Yen, Brea, CA (US); Ding Yuan Yen, Brea, CA (US)

(72) Inventors: Ding Yuan Yen, Kowloon (HK); Hsaio Wei Fang, New Taipei (TW); Te Min Lai, Taichung (TW)

( * ) Notice: Subject to any disclaimer, the term of this patent is extended or adjusted under 35 U.S.C. 154(b) by 0 days.

(21) Appl. No.: 15/438,124

(22) Filed: Feb. 21, 2017

(65) Prior Publication Data

US 2017/0245786 A1 Aug. 31, 2017

(30) Foreign Application Priority Data

Feb. 26, 2016 (CN) .......................... 2016 1 0106453

(51) Int. Cl.
| | |
|---|---|
| *G06K 9/00* | (2006.01) |
| *A61B 5/11* | (2006.01) |
| *G06T 7/00* | (2017.01) |
| *A61B 5/024* | (2006.01) |
| *A61B 5/103* | (2006.01) |
| *A61B 5/113* | (2006.01) |
| *A61B 5/00* | (2006.01) |
| *A61B 5/0205* | (2006.01) |
| *A61B 5/08* | (2006.01) |
| *G06T 7/246* | (2017.01) |

(52) U.S. Cl.
CPC .......... *A61B 5/1128* (2013.01); *A61B 5/0077* (2013.01); *A61B 5/0205* (2013.01); *A61B 5/02416* (2013.01); *A61B 5/02444* (2013.01); *A61B 5/0816* (2013.01); *A61B 5/1032* (2013.01); *A61B 5/113* (2013.01); *G06K 9/00234* (2013.01); *G06K 9/00261* (2013.01); *G06K 9/00362* (2013.01); *G06K 9/00765* (2013.01); *G06T 7/0016* (2013.01); *G06T 7/248* (2017.01); *A61B 2576/00* (2013.01); *G06T 2207/10024* (2013.01); *G06T 2207/30004* (2013.01); *G06T 2207/30076* (2013.01); *G06T 2207/30201* (2013.01)

(58) Field of Classification Search
CPC ..... A61B 5/1128; A61B 5/1032; A61B 5/113; A61B 2576/00; G06T 7/0016; G06T 7/74; G06T 2207/30201; G06T 2207/30004; G06K 9/00765; G06K 9/00261; G06K 9/00234; G06K 9/00362
See application file for complete search history.

(56) References Cited

U.S. PATENT DOCUMENTS

| 2014/0274388 A1* | 9/2014 | Nguyen | .............. G07F 17/3206 463/31 |
| 2014/0276114 A1* | 9/2014 | Maeda | ................. A61B 5/0082 600/479 |

(Continued)

*Primary Examiner* — Amir Alavi
(74) *Attorney, Agent, or Firm* — Sanford Astor

(57) ABSTRACT

The invention relates to a method for measuring the human heartbeat rate, comprising the steps of: 1) obtaining a video of the measured subject; 2) parsing the video into a series of image frames; 3) arranging the multiple generated image frames in sequential order; 4) detecting the position of the region of the face in each image; 5) obtaining the facial fluctuation frequency of the measured object according to the change of the position of the face region in the image frame system.

9 Claims, 4 Drawing Sheets

(56) References Cited

U.S. PATENT DOCUMENTS

| | | | |
|---|---|---|---|
| 2015/0126872 A1* | 5/2015 | Dubielczyk | A61B 90/39 600/473 |
| 2016/0007865 A1* | 1/2016 | Sakata | A61B 5/6898 600/480 |
| 2016/0007935 A1* | 1/2016 | Hernandez | A61B 5/7278 600/301 |
| 2016/0135706 A1* | 5/2016 | Sullivan | A61B 5/0059 600/301 |
| 2017/0112382 A1* | 4/2017 | Nakata | A61B 5/0077 |
| 2017/0245765 A1* | 8/2017 | Yen | A61B 5/02055 |
| 2017/0245786 A1* | 8/2017 | Yen | A61B 5/0077 |

* cited by examiner

S2-1, at a rate of 30 frames per second on the measured object for continuous camera, get a series of video images;

S2-2, the video image analysis uses 30 frames per second images;

S2-3, generate a 10-frame transition image in the adjacent frame image;

S2-4, using face detection on each frame image, gets face area location;

S2-5, according to the change of the position of the face region between the images, we get the human face's fluctuation frequency.

*FIG. 2*

METHOD OF MEASURING THE HEART RATE AND RESPIRATORY RATE OF A HUMAN BEING

CROSS-REFERENCE TO RELATED APPLICATIONS

This application claims priority of Chinese Patent Application No. 201610106453.1, filed on Feb. 26, 2016, the entire contents of which are hereby incorporated herein by reference.

TECHNICAL FIELD

The present invention relates to a method for measuring the life parameter of a human body, and more particularly to a method for measuring a human heartbeat rate and respiratory rate using an image recognition technique.

BACKGROUND

The invention relates to a method for measuring the human heartbeat rate, comprising the steps of: 1) obtaining a video of the measured subject; 2) parsing the video into a series of image frames; 3) arranging the multiple generated image frames in sequential order; 4) detecting the position of the region of the face in each image; 5) obtaining the facial fluctuation frequency of the measured object according to the change of the position of the face region in the image frame system. The method comprises the following steps of: parsing the video into a series of image frames to generate the multi-frame image, and slowing down the video; then obtaining the human heart and respiratory rates according to the fluctuations of the area of the face and the chest cavity in the slowed-down video, thereby obtaining long-range measurements of the human heartbeat rate and respiratory rate, and better evaluation of the subject's health.

Since heartbeat rate and respiratory rate are important parameters of human life, accurate and convenient measurement of human heartbeat rate and respiratory rate is of importance for evaluating physical health. The traditional methods of measuring the heartbeat rate of the human body having mainly been through pulse detection—the existing detection methods, including heart rate monitor and heart rate meter, require close contact of measuring devices with the measured person. The prior art (CN 101959458A) also discloses a method of measuring heartbeat rate using a visible light image by measuring a plurality of visible light images by receiving a plurality of visible light images corresponding to the skin of a subject near the blood-feeding capillary of the heart. However, the method still requires close contact with the skin of the measured object in order to obtain a clear capillary image, and the quality of image acquisition seriously affects the accuracy of the test.

With the progress of science and technology, people's heart rate, breathing, and other life parameters of the measurement also has a new requirement not yet satisfied by the existing measurement methods: long-range measurement. Thus, achieving long-range heartbeat and respiratory monitoring will be an important future direction of development.

SUMMARY

In order to solve the technical problem in the prior art that the human heart rate and the respiratory rate cannot be accurately measured remotely, the invention provides a method for long-range measuring of the human heartbeat rate and the respiratory rate based on processing the video and images acquired by the camera; and through the image recognition technology to detect changes in face and chest position, which may then be analyzed to determine the body's heartbeat rate and respiratory rate from long-range.

The technical proposal of the present invention for solving the above technical problems is as follows:

A method of measuring a human heart rate, comprising the steps of:
a) acquiring the video of the measured object;
b) parsing the video into a series of image frames;
c) arranging the multiple generated image frames in sequential order;
d) detecting the position of the region of the face in each image;
e) according to the change of the position of the face area in the image frame system, the facial fluctuation frequency of the measured object, namely the heartbeat rate of the human being, is obtained.

Furthermore, in step e), the DC component in the facial fluctuation signal is filtered and removed to obtain a periodic wave-like face fluctuation signal, or the face fluctuation frequency of the subject.

The present invention also provides another method of measuring a human heart rate, comprising the steps of:
a) acquiring the video of the measured object;
b) parsing the video image into a series of image frames;
c) arranging the multiple generated image frames in sequential order;
d) detecting the area of the face in each image;
e) analyzing the color distribution in the face area of each image;
f) according to the change of the color distribution of each frame in the image frame system, the face color change frequency of the measured object, corresponding to the heartbeat rate of the human being, is obtained.

Furthermore, the distribution of red components is counted in step e).

In addition, the present invention also provides a method for measuring the respiratory rate of a human body, comprising the steps of:
a) acquiring the video image of the measured object;
b) parsing the video image into a series of image frames;
c) arranging the multiple generated image frames in sequential order;
d) detecting the position of the region of the face in each image;
e) calculating the position of the chest region according to the position of the face region;
f) according to the change of the position of the thoracic cavity region in the image frame series, the thoracic fluctuation frequency of the measured object, corresponding to the respiratory rate of the human being, is obtained.

Furthermore, in step e), a region located 1.5 to 2.0 face lengths below the upper edge of the face is defined as the position of the chest region.

Compared with the prior art, the invention generates a slowed-down video via the parsed images of the video, and, based on the facial fluctuation frequency of the measured object and the face color change frequency of the measured object, achieves the long-range measurement of the human heartbeat rate and the respiratory rate to better evaluate the physical health of the subject

BRIEF DESCRIPTION OF THE DRAWINGS

FIG. 2 is a flow chart for measuring the heart rate in embodiment 1;

DETAILED DESCRIPTION

For the purpose of describing the principles and the technical solutions of the present invention, the following description will be made in detail with reference to the accompanying drawings. The examples are illustrative only and are not intended to limit the scope of the invention.

Heart rate is an important indicator of health. Each person's heart rate is different, with normal adult normal heart rate ranging around 60 to 100 times per minute. Normal heart rhythm is affected by many factors, when the movement of the heartbeat will speed up, rest or sleep when the heartbeat will slow down, exhaled heartbeat slower, fever, tension, excessive pressure, pain, etc., will also affect the heart rate. Heart rate is affected by breathing speed, under normal circumstances, women heart rate faster than men, normal adults breathing about 16-20 times per minute, and the heart rate is 1:4, that is, every breath, heart beat four times.

Heart beat blood flows through the contraction of the heart into the aorta, and is then passed to the systemic arteries. When the blood enters into the blood vessels of the head, the pulse will make the whole face fluctuate slightly. The amplitude of these fluctuations is quite subtle—under normal circumstances the human eye can not directly detect these subtle changes, but through the high-speed camera shooting slowed down, any slight fluctuations can be accurately captured. The present invention mainly utilizes the fluctuation of the facial area of the body when the heartbeat occurs, and then forms a fine displacement in the image. By recognizing the small displacement of the facial area in the image frame, the heartbeat can be judged and then the heartbeat rate is counted and calculated. In addition, as the heart beats, facial blood vessels will be followed by congestion, facial color will have a small change, through the capture and analysis of the camera, you can change the frequency of face color to get heart rate. Respiratory frequency measurement principle and the principle of the heart rate measurement similar to the lung and the air exchange, when the lungs inhalation of air will make the chest ups and downs, by capturing the image of the chest between the site changes to identify the occurrence of breathing, and then analyze the respiratory rate. The foregoing is an explanation of the principles of the present invention, which will be further described below with reference to examples.

Figure 1:
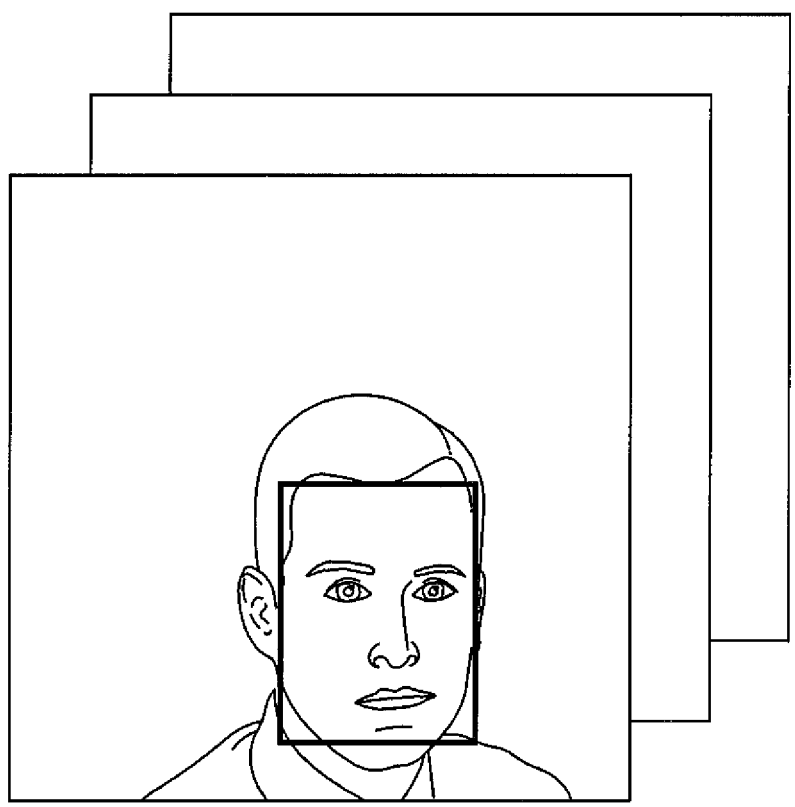
FIG. 1 is a schematic view of the present invention for detecting a face region.

The invention uses a high-definition camera to continuously photograph the measured object to obtain a series of video images, and then analyzes the video images to obtain the heart rate and the respiratory rate. In one of these methods, a series of images were taken with 1080p at 30 frames per second using an 8-megapixel wide-angle lens. The image is extracted by multi-frame image processing, 1080P image resolution of 1920×1080 about two million frames, through the face recognition program to lock the face position of each image, using the face recognition algorithm to locate the face in each image as shown in FIG. 1. Face fluctuation is an inertial motion, each about 0.2 to 0.4 seconds, in the video sequence to extract a series of images, and through the image processing method in the adjacent 10 frames inserted between the images on the video ⅒ rate release. The faces of each image are located by the face recognition algorithm, and the position of the face in the image is determined by the upper left corner and the lower right corner of the frame. The image is illustrated with 30 frames per second for example. The coordinates of the upper left corner and lower right corner of the region are as follows:

| | | | |
|---|---|---|---|
| (230, 410) (540, 660), | (230, 410) (540, 660), | (230, 410) (540, 660), | (230, 410) (540, 660), |
| (230, 410) (540, 660), | (230, 410) (540, 660), | (230, 410) (540, 660), | (230, 410) (540, 660), |
| (230, 410) (540, 660), | (231, 411) (541, 661), | (231, 411) (541, 661), | (231, 412) (541, 662), |
| (231, 412) (541, 662), | (231, 411) (541, 661), | (231, 411) (541, 661), | (230, 410) (540, 660), |
| (230, 410) (540, 660), | (230, 410) (540, 660), | (230, 410) (540, 660), | (230, 410) (540, 660), |
| (230, 410) (540, 660), | (230, 410) (540, 660), | (230, 410) (540, 660), | (230, 410) (540, 660), |
| (230, 410) (540, 660), | (230, 410) (540, 660), | (230, 410) (540, 660), | (230, 410) (540, 660), |
| (230, 410) (540, 660), | (230, 410) (540, 660) | | |

As can be seen from the above data, the measured object in the inertial oscillation direction is slightly to the top right (to the observer's point of view), from the beginning of the first 12 to 19 images for the emergence of a fluctuation, which represents a heartbeat occurs. Followed by analysis of the follow-up video frame, this can produce a count of the number of heartbeats that occur per minute, and thus the heart rate. The concrete process is shown in FIG. 2, comprising the following steps:

S2-1, at a rate of 30 frames per second on the measured object for continuous camera, get a series of video images;

S2-2, the video image analysis uses 30 frames per second images;

S2-3, generate a 10-frame transition image in the adjacent frame image;

S2-4, using face detection on each frame image, gets face area location;

S2-5, according to the change of the position of the face region between the images, we get the human face's fluctuation frequency.

In step S2-4, since the face fluctuation caused by the heartbeat is roughly one-cycle motion, the amplitude and the frequency are relatively fixed, and the DC component in the facial fluctuation signal is filtered to obtain a regular frequency of facial fluctuation.

Figure 3:
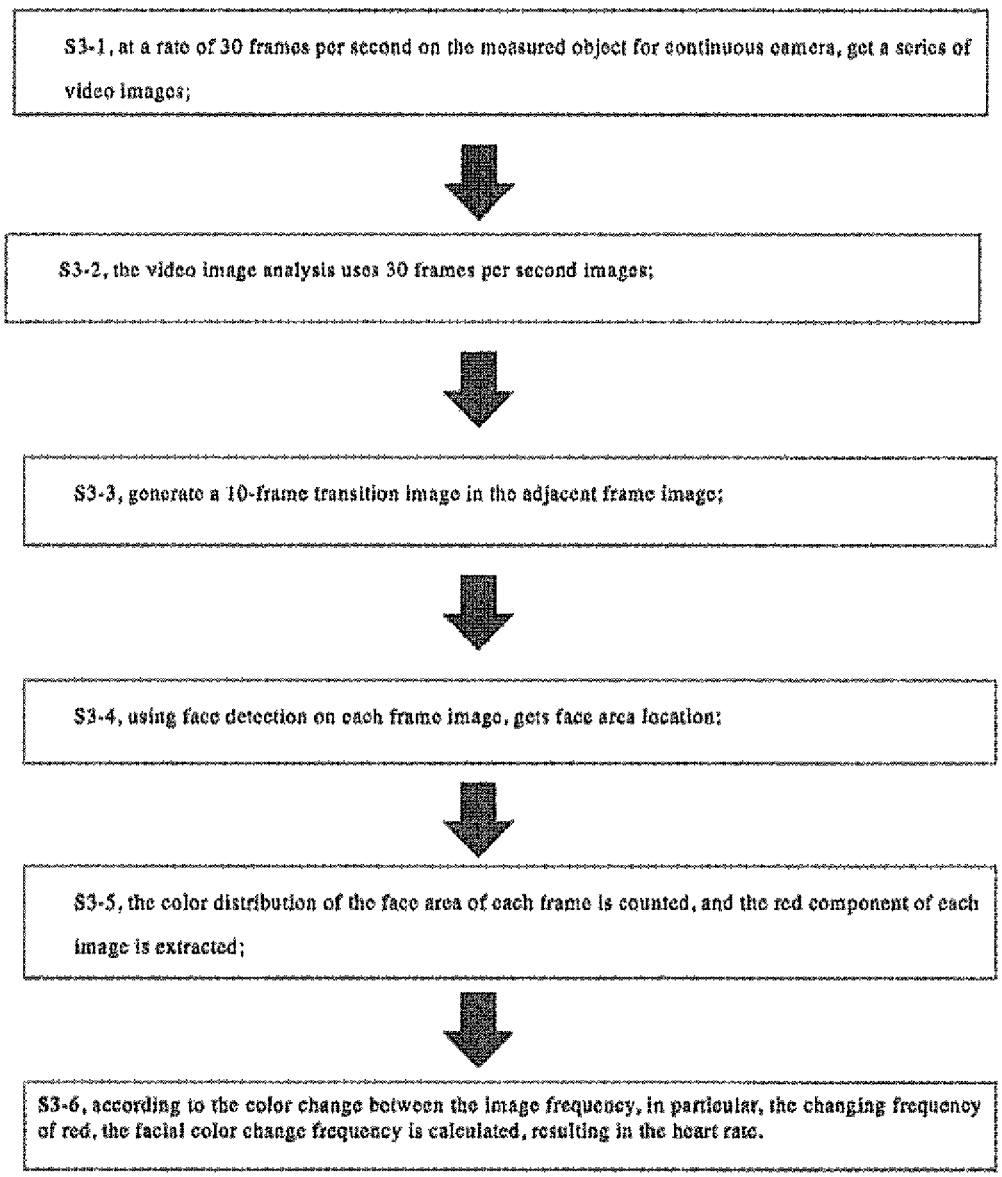
FIG. 3 is a flow chart of Example 2 for measuring the heart rate.

In addition to measuring heartbeat rate based on facial fluctuations, but also according to the face of the color distribution changes in heart rate statistics, the specific measurement steps shown in FIG. 3:

S3-1, at a rate of 30 frames per second on the measured object for continuous camera, get a series of video images;

S3-2, the video image analysis uses 30 frames per second image;

S3-3, generate a 10-frame transition image in the adjacent frame image;

S3-4, using face detection on each frame image, gets face area location;

S3-5, the color distribution of the face area of each frame is counted, and the red component of each image is extracted;

S3-6, according to the color change between the image frequency, in particular, the changing frequency of red, the facial color change frequency is calculated, resulting in the heart rate.

Figure 4:
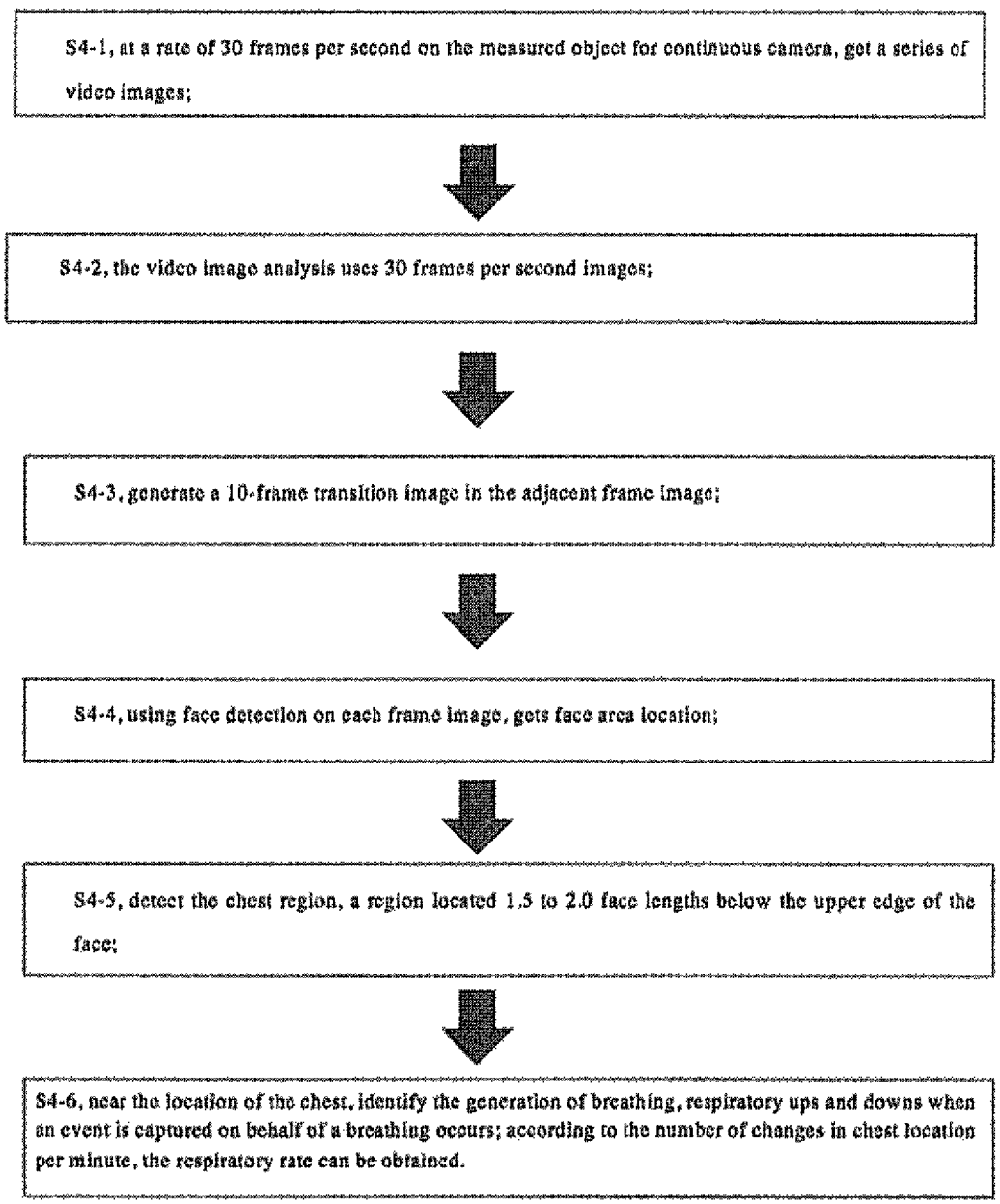
FIG. 4 is a flow chart for measuring the respiratory rate of the human body.

Breathing frequency measurement and heart rate measurement is similar to FIG. 4: extracted from the image of multi-frame image, face detection algorithm is used to determine the location of the face in each image; according to the location of the face, determine the location of the thoracic position; detect the chest region, a region located 1.5 to 2.0 face lengths below the upper edge of the face; near the location of the chest, identify the generation of breathing, respiratory ups and downs when an event is captured on behalf of a breathing occurs; according to the number of changes in chest location per minute, the respiratory rate can be obtained.

The measured human heart rate and respiratory rate can also be set up in real time and uploaded to the cloud server in the region. The user can bind the device account login and connect to the server for real-time view of the measured heart rate and respiration. Preferably, the invention further comprises a face recognition unit which records the historical heart rate and the respiratory rate data of each measured object. When it is found that the heart rate or the respiratory rate measured by the same subject has large differences from the historical measured data, this may suggest that physical condition of the measured object may be abnormal, which can be detected via remote monitoring and can trigger alerts to the users.

The foregoing description is only a few examples of the present invention and is not intended to be limiting of the present invention. Any modifications, equivalent substitutions, improvements and the like within the spirit and principles of the invention are intended to be embraced by the present invention Protection range.

What is claimed is:

1. A method of measuring the human heartbeat rate, comprising the steps of:
   a). using a high definition camera to continuously photograph the position of the face area of a human being, to obtain a series of video images;
   b). parsing the video images into a series of image frames;
   c). arranging the image frames in sequential order;
   d). detecting the position of the region of the face in each image;
   e). according to the change of the position of the face area in the image frames, the facial color fluctuation frequency of the human being, which corresponds to the heartbeat of the human being.

2. The method for measuring the heartbeat rate of a human being according to claim 1, wherein the DC component in the facial color fluctuation signal is filtered and removed to obtain a periodic wave-like facial color fluctuation signal, or the facial color fluctuation frequency of the human being.

3. The method of measuring the heart rate of a human being, comprising the steps of:
   a). using a high-definition camera to continuously photograph in the position of the face area of a human being, to obtain a series of video images;
   b). parsing the video images into a series of image frames;
   c). arranging the image frames in sequential order;
   d). detecting the area of the face in each image;
   e). analyzing the color distribution in the face area of each image;
   f). the change of the face color distribution of each image and the change of frequency of each image corresponds to the heartbeat of the human being.

4. The method for measuring the heart rate of a human being according to claim 3, in which the face color is red.

5. The color distribution of the face area of each frame of claim 4, is counted and the red component of each image is extracted and calculated, resulting in the heart rate.

6. The facial color change between the image frequency of red in claim 4, is calculated, resulting in the heart rate.

7. The high-definition camera of claim 3 has a rate of 30 frames per second and gets a series of video images of 30 frames per second.

8. A method of measuring the frequency of breathing in a human body, comprising the steps of:
   a). using a high-definition camera to continuously photograph in the position of the face area of a human being, to obtain a series of video images;
   b). parsing the video images into a series of image frames;
   c). arranging the image frames in sequential order;
   d). detecting the area of the face in each image;
   e). according to the location of the face in each image, determine the location of the thoracic position and detect the chest region, below the upper edge of the face near the location of the chest;
   f). according to the change of the position of the thoracic region in the image frames, the respiratory rate of the human being is obtained, by the number of changes in the chest region per minute.

9. The method for measuring the breathing frequency of a human body according to claim 8, in which a region located 1.5 to 2.0 face lengths below the upper edge of the face is defined as the position of the chest region.

* * * * *